United States Patent [19]

Thompson

[11] 4,287,886
[45] Sep. 8, 1981

[54] REMOTE PRESSURE SENSOR TUBE FOR THE ALARM SYSTEM OF A RESPIRATOR

[76] Inventor: Harris A. Thompson, 175 Bellevue Dr., Boulder, Colo. 80302

[21] Appl. No.: 148,766

[22] Filed: May 12, 1980

[51] Int. Cl.³ .............................................. A61M 16/00
[52] U.S. Cl. ............................ 128/202.22; 128/205.23
[58] Field of Search ...................... 128/202.22, 204.23, 128/204.26, 205.23

[56] References Cited

U.S. PATENT DOCUMENTS

| 3,333,584 | 8/1967 | Andreasen et al. | 128/202.22 |
| 3,867,934 | 2/1975 | Ollivier | 128/202.22 |
| 3,906,934 | 9/1975 | Haverland | 128/202.22 |
| 4,067,329 | 1/1978 | Winicki | 128/202.22 |
| 4,096,858 | 6/1978 | Eyrick et al. | 128/202.22 |
| 4,155,357 | 5/1979 | Dahl | 128/202.22 |

Primary Examiner—Henry J. Recla
Attorney, Agent, or Firm—Klaas & Law

[57] ABSTRACT

In artificial respiration apparatus of the type which uses a breathing tube extended from the apparatus to a patient. An alarm system is incorporated into the apparatus which responds to a disruption of the cyclic air pressures therein through connection with an air supply passageway in the respirator. The invention uses a sensor tube, extended from the respirator apparatus to the remote end of the breathing tube. This sensor tube connects with the alarm system so it may respond to a disruption of the cyclic pressures at this remote end of the breathing tube. A selector valve at the respirator apparatus connects the alarm system with either the air supply passageway in the apparatus or with the sensor tube. The sensor tube terminates as a jack which is inserted into a socket in the selector valve. The alarm responds to pressures in the air supply passageway when the jack is not in the socket. However, the alarm responds to pressures in the sensor tube when the jack is inserted into the socket.

7 Claims, 6 Drawing Figures

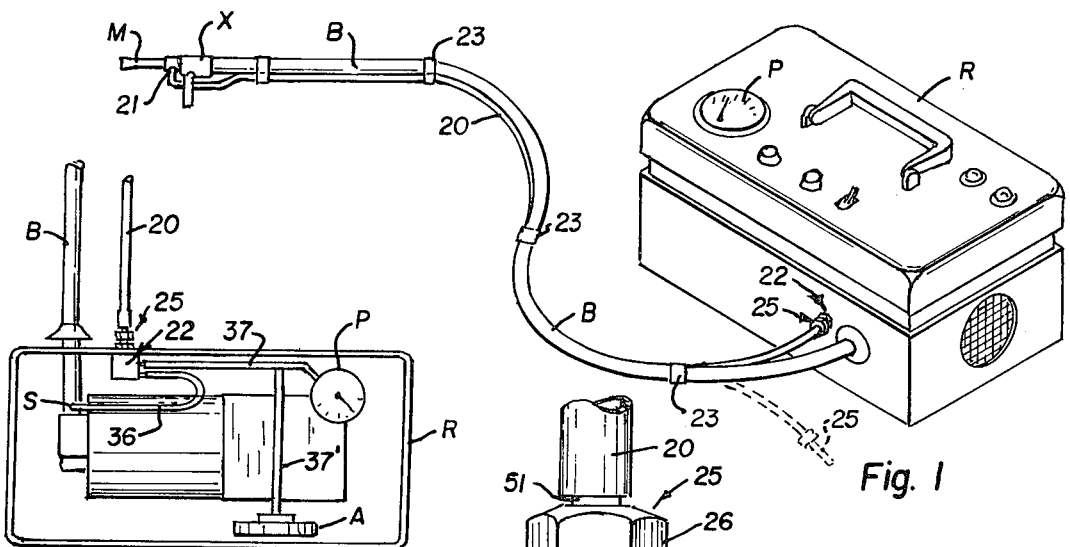
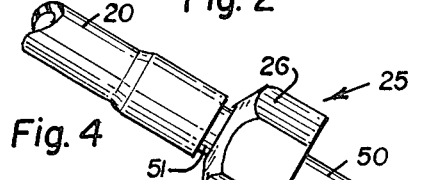
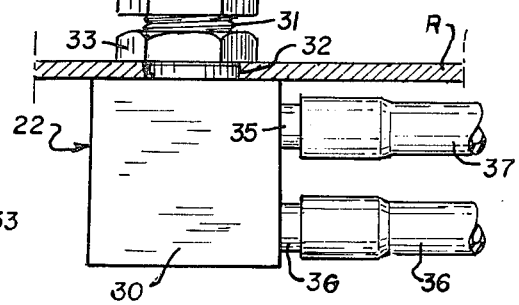
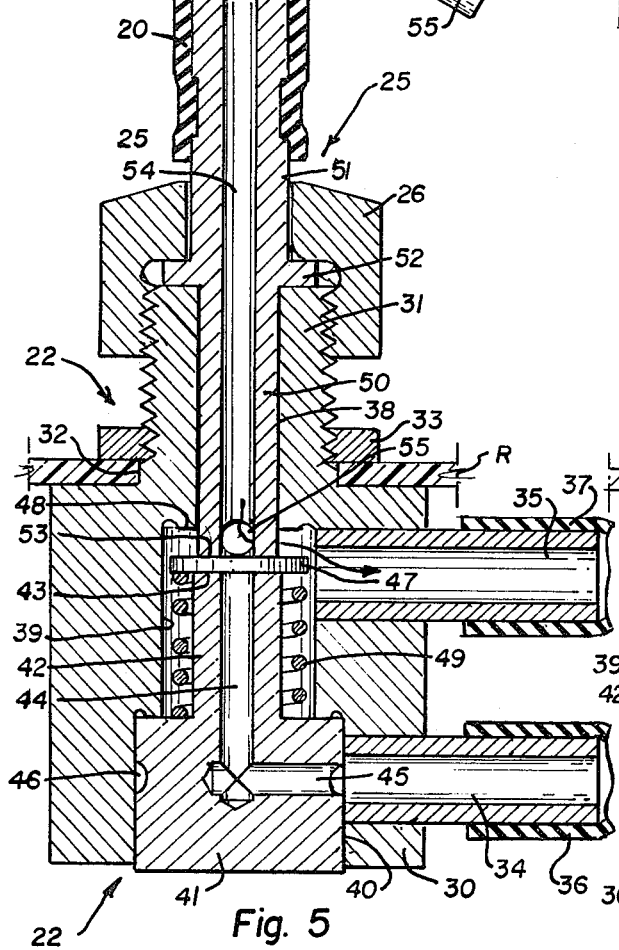
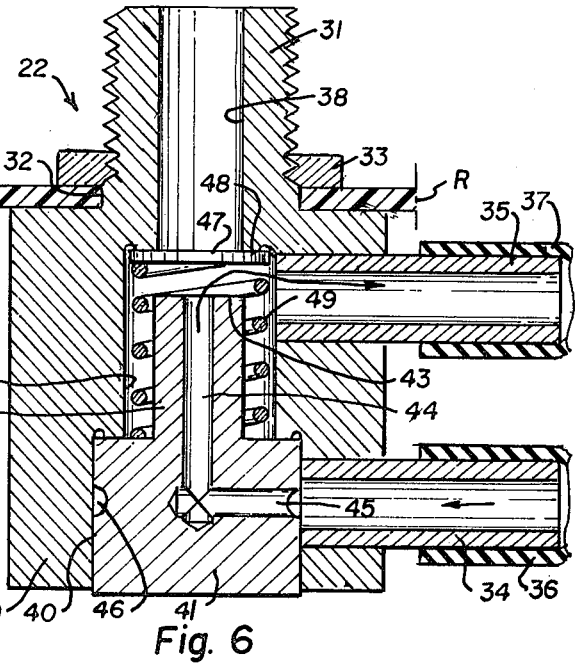

REMOTE PRESSURE SENSOR TUBE FOR THE ALARM SYSTEM OF A RESPIRATOR

The present invention relates to artificial respiration apparatus, and more particularly to respirators of the type which use a breathing tube extending from the respirator and to a patient.

The invention is a remote pressure sensor tube for the alarm system of a respirator to actuate the alarm whenever an improper pressure action occurs at the extended end of the breathing tube. For example, the remote end of the sensor tube may be connected to a mouthpiece or a track adaptor and the other end of the tube is connected with the alarm system within the respirator.

It follows that a primary object of the invention is to provide a novel and improved remote sensor tube for the alarm system of a respirator which will set off an alarm if a misfunction in the cyclic respiration action occurs at the remote end of the breathing tube. The need for this sensor tube was brought about by the fact that a patient may drop his mouthpiece, a track adaptor may be disconnected, or the airflow in the breathing tube may become blocked. The remote sensor is especially important since such accidents are not always sensed by the regular alarm system within the respirator apparatus which monitors air pressure within the apparatus near the breathing tube connection.

Other objects of the invention are to provide a novel and improved remote pressure sensor tube for the alarm system within a respirator which will shift the alarm indicator control from the respirator and to the patient; can be quickly and easily incorporated into regular respirators; can be used with positive and negative pressure respirators; can be quickly and easily connected and disconnected to and from a respirator without disrupting the normal operation of the respirator whenever it is disconnected therefrom; and, is a neat appearing, low-cost, reliable and durable addition to a respirator.

With the foregoing and other objects in view, my invention comprises certain constructions, combinations and arrangements of parts and elements as hereinafter described, defined in the appended claims and illustrated in the accompanying drawings in which:

FIG. 1 is an isometric view of a respirator having a breathing tube and a remote pressure sensor tube extended therefrom according to the present invention;

FIG. 2 is a diagrammatic sectional view of the respirator to illustrate air pressure indicator leads, a directional valve within the respirator and also the manner in which the end of the sensor tube connects with the directional valve;

FIG. 3 is an enlarged portion of FIG. 2 showing the directional valve, portions of pressure indicator leads connected thereto and the end of the sensor tube being connected to this directional valve;

FIG. 4 is a view of the end portion of the pressure sensor tube as it appears when disconnected from the directional valve;

FIG. 5 is an enlarged sectional view of the components as shown in FIG. 3 to better illustrate the passageways through the directional valve and end of the sensor tube connected thereto; and FIG. 6 is a sectional view, similar to FIG. 5, but with the sensor tube removed.

Referring more particularly to the drawing, the respirator R shown at FIG. 1, may be of any type which uses a breathing tube B to extend to a patient. In conventional arrangements various connective devices may be used at the extended end of the tube, the drawing showing a mouthpiece M and an exhalation valve X. A trach adaptor or other device, not shown, may also be used.

A pressure gage P and an alarm A (FIG. 2) are normally included in a conventional respirator. The pressure gage P registers the cyclic pressure fluctuations at an air supply passageway S within the respirator to which the breathing tube connects. At least one trigger circuit of the alarm is also controlled by such cyclic pressure fluctuations in the air supply passageway S. Since the pressure of airflow into the breathing tube is cyclic, the trigger circuit within the alarm is sensed to respond to a failure of proper cyclic pressure variations, or more simply, it may be sensed to respond to a failure of a selected maximum, or minimum, pressure at proper time intervals.

It has been found that accidents can occur at the extended end of the breathing tube which will not trigger the alarm when the respirator itself is operating properly. A patient may faint or otherwise drop a breathing tube. If a trach adaptor is used, it may become disconnected. Also, the breathing tube itself may be obstructed. To avoid an alarm failure when such accidents happen, the present invention uses pressure fluctuations at the extended end of the breathing tube to trigger the alarm.

The present invention includes a remote pressure sensor tube 20, one end of which is connected in a Tee 21 located at the extended end of the breathing tube as between the mouthpiece M and the exhalation valve X. The other end of the sensor tube 20 is connected to a selector valve 22 mounted in the case of the respirator R. This sensor tube 20 need not have a large diameter since no significant airflow will occur in it. It is of flexible material and may be conveniently attached to the breathing tube B by suitable clips 23 as shown at FIG. 1 to provide for a neat appearing arrangement.

It is desirable to have the remote pressure sensor to be connectable and disconnectable from the respirator at the user's option. When the sensor tube is connected to the respirator, the pressure gage P and the alarm A must be connected with the sensor tube 20 to respond to pressures at the extended end of the breathing tube. However, when the tube is disconnected from the respirator, the pressure gage P and the alarm A must be connected to the supply passageway S within the respirator as shown in FIG. 2. Thus, the selector valve 22 is a three-way-type valve adapted to operate automatically responsive to the connection and disconnection of the sensor tube 20, the end of the sensor tube carrying a connector jack 25 and a holding nut 26 as hereinafter further described.

The selector valve 22 is formed as a block-like body 30 having a threaded stub 31 extending from one end, which passes through a suitable hole 32 in the respirator box wall. A lock nut 33 turned onto this stub 32 holds the valve 22 in place with the body 30 being within the respirator and the stub 32 projecting from the side of the respirator to receive the jack 25. Two tubular nipples 34 and 35 project from a side of this body 30 to define passageways in the valve for connection with tubular leads 36 and 37. The nipple 34 connects with the lead 36 which extends to the aforementioned supply passageway S of the respirator. The nipple 35 connects with the lead 37 which extends to the pressure gage P and also bifurcates to provide a lead 37' which extends to the alarm A as shown at FIG. 2.

A stepped passageway is extended through the selector valve 22 which is axially aligned with the stub 31. The smaller portion of this passageway, through the stub 31, forms a socket 38 to receive the connector jack 25. An intermediate chamber 39 is formed in the body 30 which connects with the side passageway formed by the tubular nipple 35. A larger socket 40 is formed in the end of the body 30 opposite the stub end and this socket 40 connects with the side passageway formed by the tubular nipple 34.

A cylindrical Tee block 41 is formed with its base tightly fitted into the socket 40. A smaller leg portion 42 of this block 41 extends partway into the chamber 39 with a squared end 43 forming a seat surface in the chamber. An axial passageway 44 in the leg joins a lateral passageway 45 in the base portion which, in turn, connects with the side passageway formed by the tubular segment 34. This connection is assured by a circumferential slot 46 about the wall of the base as shown in FIGS. 5 and 6.

A valve disc 47 is located in the space between the end 43 of the leg portion and the juncture between the socket 38 and chamber 39. This juncture is squared to form a seat 48 against which the disc 47 seats when the connector jack 25 is not in the socket 38. A spring 49 about the leg portion 42 then urges the disk 47 against this seat 48 as shown at FIG. 6. When the disc 47 is so positioned, the pressure gage P and the alarm A respond to pressures at the air supply passageway S within the respirator. The response is through the lead 36, the block passageways 45 and 44 and the leads 37 and 37' from the valve 22.

The jack 25 is a tubular member formed as two segments, a sleeve 50 which fits into the socket 38 of the selector valve and a tube connector 51 which connects with the sensor tube 20. A circumferential shoulder 52 is formed at the juncture of these segments and this shoulder 52 butts against the end of the stub 31 of the selector valve 22. The holding nut 26 is fitted upon the tube connector segment 51 and when it is turned onto the stub 31, the shoulder 52 is tightly fitted against the stub 31 as shown at FIG. 5.

The end of the sleeve 50 is squared to form a seat 53 and its length is such that with the jack connected in the stub, the seat 53 presses the disc 47 against the seat 43 of the leg 42 as shown at FIG. 5. This closes the passageway 44, closing off the communication of pressure indications at the air supply passageway S within the respirator. At the same time, pressure indications from the remote end of the sensor tube 20, as at Tee 21 are communicated to the pressure gage P and alarm A through the tube 20, through a longitudinal passageway 54 in the jack 25, through an orifice 55 adjacent to the sleeve seat 53 and thence through the leads 37 and 37'.

It follows that whenever the sensor tube 20 is connected to the respirator R, by connection of the jack 25 to the selector valve 22, the pressure gage P indicates pressure at the remote end of the sensor tube, normally at the breathing tube and the alarm A responds to loss of pressure or improper pressures at this remote point. However, as heretofore described, whenever the sensor tube is removed from the selector valve 22, the pressure gage and alarm function in a conventional manner responding to pressure failure or improper pressures at the air supply passageway S within the respirator.

I have now described my invention in considerable detail. However, it is obvious that others skilled in the art can build and devise alternate and equivalent constructions which are nevertheless within the spirit and scope of my invention. Hence, I desire that my protection be limited, not by the constructions illustrated and described, but only by the proper scope of the appended claims.

What is claimed is:

1. In combination with a respirator having a breathing tube extended therefrom and to a mouthpiece or the like at its remote end and having a pressure-responsive indicator means, including an alarm, to indicate a disruption of the pressures of cyclic respiratory action within a supply passageway in the respirator, the improvement comprising: a sensor means associated with the breathing tube and with the indicator means to initiate a pressure indication at the indicator means responsive to a disruption of pressures of cyclic respiratory action at the remote end of the breathing tube, and selective switch-over means adapted to permit the indicator means to selectively respond to a disruption within the respirator or to a disruption at the remote end of the breathing tube.

2. In the combination defined in claim 1 wherein: said sensor means is a sensor tube having its remote end connected to the remote end of the breathing tube and having its other end connected with the indicator means at the respirator.

3. The combination defined in claim 2, wherein: the sensor tube connects with a three-way selector valve means at the respirator adapted to connect the tube passageway with the indicator means and cut off the pressure indications within the respirator and to alternately disconnect the tube passageway from the indicator means and to cut in the pressure indications within the respirator.

4. The combination defined in claim 2 including (a) a selector valve at the respirator, (b) a first circuit through the selector valve from the supply passageway in the respirator to the indicator means; (c) a second circuit through the selector valve from the sensor tube to the indicator means; and (d) valving means within the selector valve to selectively close one circuit and open the other whereby the indicator means may be responsive to the pressure indications in the supply passageway or in the sensor tube.

5. The combination defined in claim 4 wherein said sensor tube terminates as a jack and said selector valve includes a socket to receive this jack.

6. The combination defined in claim 5 wherein said valving means is adapted to close off the sensor tube passageway and open the supply passageway when the sensor tube jack is removed from the socket and to close off the supply passageway and open the sensor tube passageway when the sensor tube jack is inserted into the socket.

7. In the combination defined in claim 6 wherein said valving means includes; a first seat at the base of the socket; a second seat in spaced opposition to the first with said supply passageway extended through this seat; a valve disc means between the first and second seats; means to urge the valve disc means against this first seat whenever the sensor tube jack is removed from the socket, with the supply passageway then being open; and wherein said valve disc means is engaged by and moved from said first seat and against said second seat whenever the sensor tube jack is inserted into the socket, with the sensor tube passageway then being open.

* * * * *